(12) United States Patent
Kariathungal et al.

(10) Patent No.: US 8,254,648 B2
(45) Date of Patent: Aug. 28, 2012

(54) METHOD FOR PROVIDING ADAPTIVE HANGING PROTOCOLS FOR IMAGE READING

(75) Inventors: Murali Kumaran Kariathungal, Hoffman Estates, IL (US); Prakash Mahesh, Hoffman Estates, IL (US); Mark Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 1204 days.

(21) Appl. No.: 11/619,915

(22) Filed: Jan. 4, 2007

(65) Prior Publication Data

US 2008/0166070 A1    Jul. 10, 2008

(51) Int. Cl.
G06K 9/00   (2006.01)
G06F 17/00  (2006.01)
G06F 3/00   (2006.01)

(52) U.S. Cl. ......... 382/128; 382/100; 715/700; 715/200
(58) Field of Classification Search .................. 382/100, 382/128
See application file for complete search history.

(56) References Cited

U.S. PATENT DOCUMENTS

| 5,808,908 | A  * | 9/1998  | Ghahramani ................ 702/182 |
| 6,237,138 | B1 * | 5/2001  | Hameluck et al. ............ 717/128 |
| 6,243,095 | B1 * | 6/2001  | Shile et al. ..................... 715/854 |
| 6,526,526 | B1 * | 2/2003  | Dong et al. ..................... 714/46 |
| 6,707,476 | B1 * | 3/2004  | Hochstedler ................. 715/789 |
| 6,904,161 | B1 * | 6/2005  | Becker et al. ................ 382/128 |
| 7,131,134 | B2 * | 10/2006 | Trovato et al. ................ 725/46 |
| 7,184,918 | B2 * | 2/2007  | Hamilton et al. ............ 702/120 |
| 7,259,729 | B2 * | 8/2007  | Shastri et al. ................ 345/1.3 |
| 7,525,554 | B2 * | 4/2009  | Morita et al. ................ 345/619 |
| 7,554,522 | B2 * | 6/2009  | Sinclair et al. ............... 345/156 |
| 7,576,757 | B2 * | 8/2009  | Kariathungal et al. ....... 345/637 |
| 7,657,566 | B2 * | 2/2010  | Mathavu et al. ............. 382/130 |
| 7,685,034 | B1 * | 3/2010  | Mori et al. ..................... 705/31 |
| 7,689,447 | B1 * | 3/2010  | Aboujaoude et al. .......... 705/7 |
| 7,698,173 | B1 * | 4/2010  | Burge et al. ................... 705/26 |
| 2002/0080181 | A1 * | 6/2002  | Razdow et al. ............ 345/772 |
| 2002/0101436 | A1 * | 8/2002  | Shastri et al. ................ 345/619 |
| 2003/0214943 | A1 * | 11/2003 | Engstrom et al. ............ 370/353 |
| 2004/0010328 | A1 * | 1/2004  | Carson et al. .................. 700/90 |
| 2004/0082845 | A1 * | 4/2004  | Matsumoto et al. ......... 600/407 |
| 2004/0202387 | A1 * | 10/2004 | Yngvesson .................. 382/305 |
| 2004/0228616 | A1 * | 11/2004 | Miyasato et al. .............. 386/83 |
| 2005/0007616 | A1 * | 1/2005  | Sugiyama et al. .......... 358/1.13 |

(Continued)

OTHER PUBLICATIONS

Moise et al, "Workflow Oriented Hanging Protocols for Radiology Workstation", Medical Imaging 2002, Proceedings of SPIE vol. 4685 pp. 189-199.*

Primary Examiner — Chan S Park
Assistant Examiner — Avinash J Yentrapati
(74) Attorney, Agent, or Firm — Hanley, Flight, Zimmerman, LLC

(57) ABSTRACT

Embodiments of the presently described technology provide a method for adapting a hanging protocol based on an efficiency of use. The method includes monitoring usage information for a hanging protocol, determining a productivity factor based on an efficiency of a first user during a reading of an imaging study, and recommending at least one of a hanging protocol selection and a hanging protocol change to a second user based on the productivity factor. The usage information includes at least one of a selection of a hanging protocol and a change to the hanging protocol by a first user during the reading of the imaging study.

14 Claims, 4 Drawing Sheets

U.S. PATENT DOCUMENTS

| | | |
|---|---|---|
| 2005/0129331 A1* | 6/2005 | Kakiuchi et al. ............... 382/275 |
| 2005/0180611 A1* | 8/2005 | Oohashi et al. ............... 382/118 |
| 2005/0267972 A1 | 12/2005 | Costa-Requena et al. |
| 2005/0289561 A1* | 12/2005 | Torres et al. ................... 719/328 |
| 2006/0111937 A1* | 5/2006 | Yarger et al. ...................... 705/2 |
| 2006/0129829 A1* | 6/2006 | Aaron et al. .................. 713/182 |
| 2006/0139312 A1* | 6/2006 | Sinclair et al. ................ 345/156 |
| 2006/0146071 A1* | 7/2006 | Morita et al. ................. 345/619 |
| 2006/0229748 A1* | 10/2006 | Yarger et al. ...................... 700/83 |
| 2006/0235732 A1* | 10/2006 | Miller et al. ....................... 705/7 |
| 2007/0005419 A1* | 1/2007 | Horvitz et al. .................. 705/14 |
| 2007/0027985 A1* | 2/2007 | Ramany et al. ............... 709/224 |
| 2007/0159962 A1* | 7/2007 | Mathavu et al. ............... 370/219 |
| 2007/0203981 A1* | 8/2007 | Takano et al. ................. 709/204 |
| 2007/0300174 A1* | 12/2007 | Macbeth et al. ............... 715/772 |
| 2008/0044069 A1* | 2/2008 | DuGal .......................... 382/128 |
| 2008/0235730 A1* | 9/2008 | Guillorit ......................... 725/44 |
| 2008/0260253 A1* | 10/2008 | Miyazaki ...................... 382/190 |
| 2008/0306775 A1* | 12/2008 | Bodlaender et al. .............. 705/3 |
| 2009/0129644 A1* | 5/2009 | Daw et al. ..................... 382/128 |
| 2009/0219159 A1* | 9/2009 | Morgenstern ............. 340/573.1 |
| 2010/0082125 A1* | 4/2010 | Pingel et al. ..................... 700/47 |
| 2010/0135543 A1* | 6/2010 | Weese et al. .................. 382/128 |

* cited by examiner

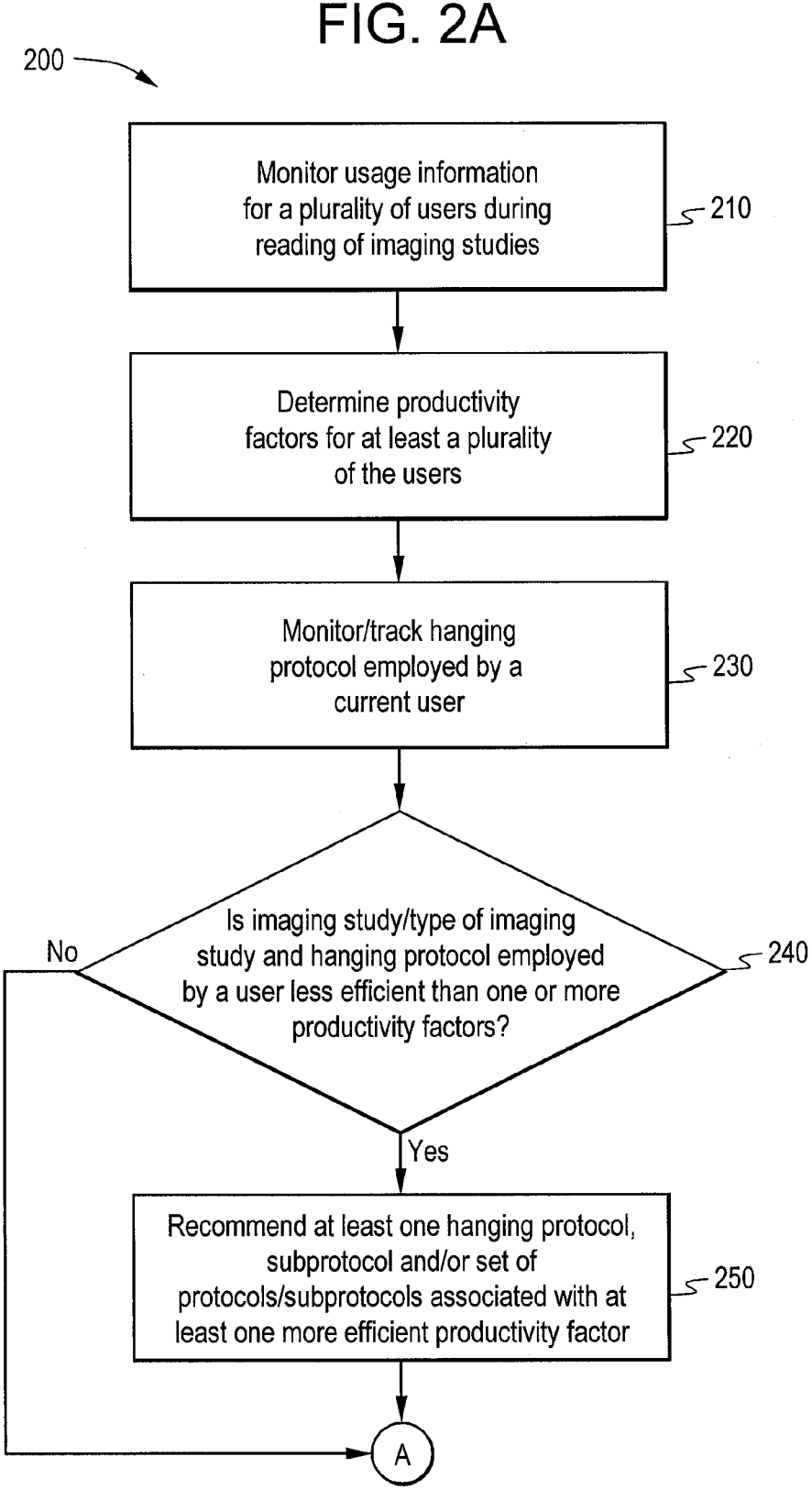

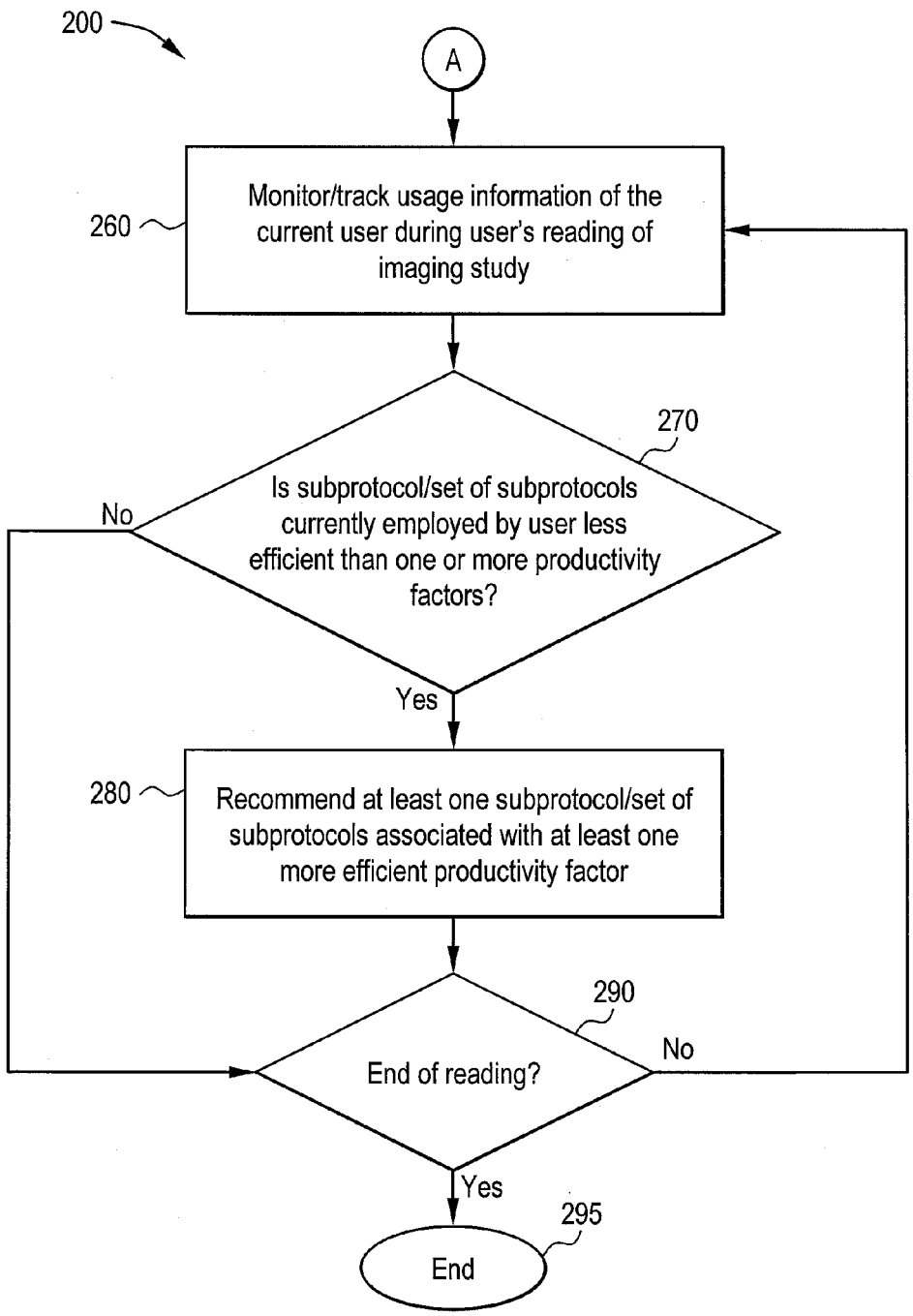

METHOD FOR PROVIDING ADAPTIVE HANGING PROTOCOLS FOR IMAGE READING

BACKGROUND OF THE INVENTION

The present invention generally relates to an improvement in the efficiency of reviewing imaging studies using hanging protocols. Specifically, the present invention relates to the adaptive and dynamic modification of hanging protocols based on other users' productivity and efficiency.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide one or more imaging studies (each including a series of images) to a display workstation. The imaging studies can include current or recently acquired images. The imaging studies can also include older or previously acquired images. Such imaging studies are referred to as historical imaging studies.

The workstation can display the images in the imaging study to a radiologist in order to permit the radiologist to perform a diagnostic examination. The review or analysis of images in an imaging study is referred to as reading the imaging study. Based on the presentation of the images in the imaging study, the radiologist can provide a diagnosis. For example, the radiologist can diagnose a tumor or lesion in x-ray images of a patient's lungs.

The images in an imaging study typically are displayed in a particular spatial layout and/or temporal sequence. In other words, the images may be displayed in certain positions on a display device relative to each other (a spatial layout, for example). The images may also be displayed in a certain ordered sequence by displaying image A first, followed by image B, followed by image C, and so on (a temporal sequence, for example). The spatial and/or temporal presentation of images is directed by a set of display rules. A display rule may include a set of instructions stored on a computer-readable media that direct the presentation of images on a display workstation. A set of display rules is known as a hanging protocol. In general, a hanging protocol is a series of display rules that dictate the spatial and/or temporal layout and presentation of a plurality of images. Existing hanging protocols are either hard coded or static, as the hanging protocols are unable to adapt to changes made by a user while reading an imaging study.

A hanging protocol for radiology workstations can rely on the following factors to layout the images in an imaging study: (a) imaging modality (modalities-in case of multi-modality hanging protocol) used to obtain images in the study, (b) body part or anatomy imaged in the study, (c) imaging procedure used to obtain the images of the study, (d) the resolution of the workstation (for example, the number of monitors) and (e) the number of historical imaging studies. In most cases, a single hanging protocol is not enough for a radiologist to read the complete study, since the study contains a number of series. That is, a particular hanging protocol is unlikely to be suitable for all reviews and analyses of imaging studies. For example, some hanging protocols may not present side-by-side comparisons of current and historical imaging studies, while other hanging protocols may provide such a presentation. The "side-by-side presentation" protocols can be better suited for certain imaging studies and analyses, while the other protocols may not.

In addition, users of a given hanging protocol may desire to alter or change the hanging protocol. For example, a user may wish to include additional display rules to alter or modify a presentation of images at a display device. For example, the user may wish to present additional images adjacent to currently displayed images. In another example, the user may wish to present additional images after the current images are reviewed. Users may also wish to remove some of the display rules of the hanging protocol, or review information in addition to that included in the hanging protocol. For example, a user may desire to review a historical imaging study not originally included in the hanging protocol.

With increasing volumes of examinations and images, a reduction of radiologists and mounting pressures on improved productivity, radiologists are in dire need of increasing their efficiency in reading imaging studies. In a given enterprise, some experienced users learn and develop particular hanging protocols and changes to existing hanging protocols that increase the efficiency of the users in reading imaging studies. However, other users have not learned or developed such hanging protocols and hanging protocol changes. These other users typically are much less efficient that the users who have learned and developed the more efficient hanging protocols.

Thus a need exists for increasing the efficiency of users reading imaging studies in an enterprise. Such a need can be met by monitoring the efficiency of users of hanging protocols during their reading of imaging studies. By determining which hanging protocols and changes to the hanging protocols results in increased user efficiency, the efficiency of additional users can be increased. For example, the efficiency of users can be improved upon by adapting hanging protocols through the monitoring of the users' selection of protocols and/or changes to the protocols along with the users' efficiencies in completing their analyses on the imaging studies. In other words, by monitoring what other, more efficient users are doing, the efficiency of the less-efficient users can be increased.

BRIEF SUMMARY OF THE INVENTION

Embodiments of the presently described technology provide a method for adapting a hanging protocol based on an efficiency of use. The method includes monitoring usage information for a hanging protocol, determining a productivity factor based on an efficiency of a first user during a reading of an imaging study, and recommending at least one of a hanging protocol selection and a hanging protocol change to a second user based on the productivity factor. The usage information includes at least one of a selection of a hanging protocol and a change to the hanging protocol by a first user during the reading of the imaging study.

Embodiments of the presently described technology also provide a computer-readable storage medium comprising a set of instructions for a computer. The set of instructions include a monitor routine, a productivity routine and a recommendation routine. The monitor routine is configured to monitor usage information for a hanging protocol, where the usage information includes at least one of a selection of a hanging protocol and a change to the hanging protocol by a first user during a reading of an imaging study. The productivity routine is configured to determine a productivity factor based on an efficiency of the first user during the reading of the imaging study. The recommendation routine is configured to recommend at least one of the hanging protocol selection and the hanging protocol change to a second user based on the productivity factor.

Embodiments of the presently described technology also provide a method for increasing an efficiency of reading imaging studies. The method includes recommending at least one of a hanging protocol and a hanging protocol change to a user based on a measured productivity of at least one other user.

BRIEF DESCRIPTION OF SEVERAL VIEWS OF THE DRAWINGS

FIGS. 2A and 2B illustrate a flowchart for a method for adapting or recommending a hanging protocol based on the efficiencies of a plurality of users employing hanging protocols and/or subprotocols to read imaging studies, in accordance with an embodiment of the presently described technology.

Figure 1:
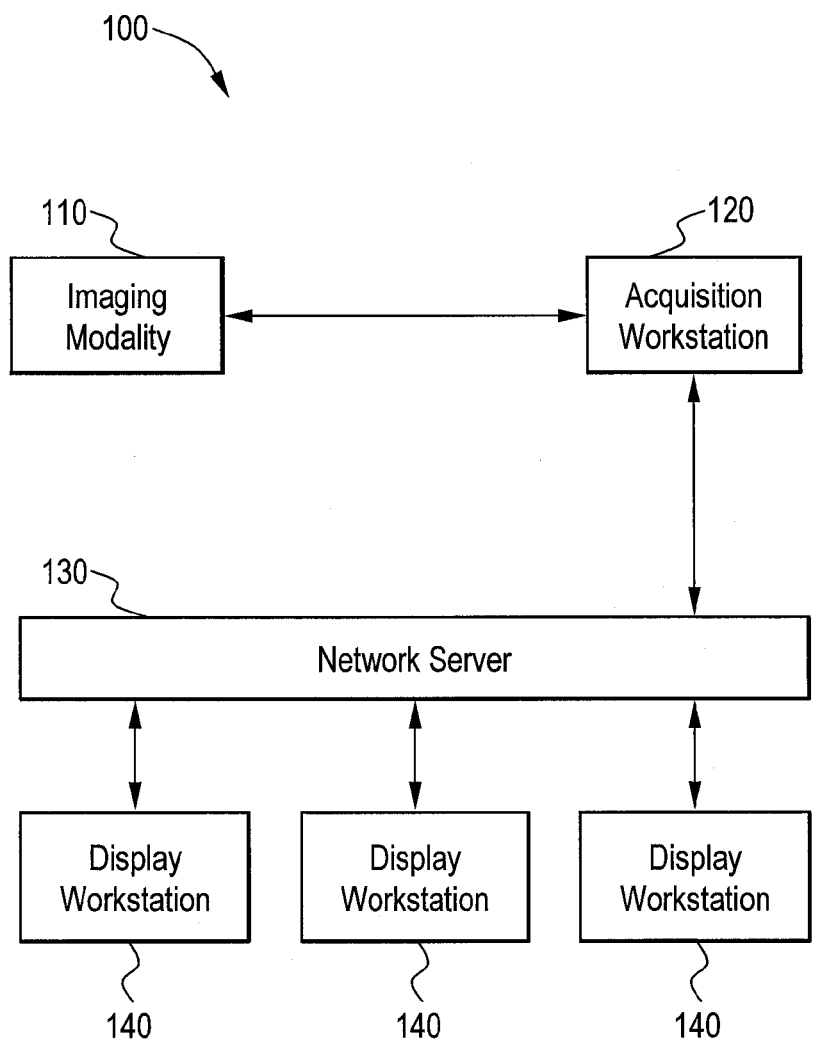
FIG. 1 illustrates an exemplary PACS system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an exemplary PACS system 100 in accordance with an embodiment of the present invention. PACS system 100 includes an imaging modality 110, an acquisition workstation 120, a network server 130, and one or more display workstations 140. System 100 can include any number of imaging modalities 110, acquisition workstations 120, network servers 130 and display workstations 140 and is not in any way limited to the embodiment of system 100 as illustrated in FIG. 1.

In operation, imaging modality 110 obtains one or more images of a patient anatomy. For example, imaging modality 110 can obtain a one, two, three or other dimensional image of a patient anatomy. Alternatively, imaging modality 110 can obtain a plurality of images or image data that is later converted into a three or more dimensional image of a patient anatomy. Imaging modality 110 can include any device capable of capturing an image of a patient anatomy such as a medical diagnostic imaging device. For example, imaging modality 110 can include an X-ray imager, ultrasound scanner, magnetic resonance imager, or the like. Image data representative of the image(s) is communicated between imaging modality 110 and acquisition workstation 120. The image data can be communicated electronically over a wired or wireless connection.

Acquisition workstation 120 can apply one or more preprocessing functions to the image data in order to prepare the image for viewing on a display workstation 140. For example, acquisition workstation 120 may convert raw image data into a DICOM standard format or attach a DICOM header. The preprocessing functions can be characterized in that they can be modality specific enhancements (for example, contrast or frequency compensation functions specific to a particular X-ray imaging device, for example) applied at the beginning of the imaging and display chain.

The image data may then be communicated between acquisition workstation 120 and network server 130. The image data can be communicated electronically over a wired or wireless connection.

Network server 130 can include a computer-readable storage medium suitable for storing the image data for later retrieval and viewing at a display workstation 140. Network server 130 can also include one or more software applications for additional processing and/or preprocessing of the image data by one or more display workstations 140, as described below.

One or more display workstations 140 are capable of or configured to communicate with server 130. Display workstations 140 can include a general purpose processing circuit, a network server 130 interface, a software memory, and an image display monitor. The network server 130 interface may be implemented as a network card connecting to a TCP/IP based network, but may also be implemented as a parallel port interface, for example.

Display workstations 140 may retrieve or receive image data from server 130 for display to one or more users. For example, a display workstation 140 may retrieve or receive image data representative of a computed radiography ("CR") image of a patient's chest. A radiologist may then examine the image as displayed on a display device for any objects of interest such as, for example, tumors, lesions, etc.

Display workstations 140 are also capable of or configured to retrieve and/or receive one or more hanging protocols from server 130. For example, a default hanging protocol may be communicated to display workstation 140 from server 130. A hanging protocol may be communicated between server 130 and a display workstation 140 over a wired or wireless connection, for example.

In general, display workstations 140 may present images representative of image data retrieved and/or received from server 130. Display workstations 140 may present the images according to a hanging protocol. For example, a hanging protocol can include a set of computer-readable instructions (or display rules, for example) that direct a computer to display a plurality of images in certain locations on a display device and/or display the plurality of images in a certain sequence or order. In another example, a hanging protocol can include a set of computer-readable instructions that direct a computer to place a plurality of images in multiple screens and/or viewports on a display device. In general, a hanging protocol can be employed to present a plurality of images for a diagnostic examination of a patient anatomy featured in the images.

A hanging protocol may direct, for example, a display workstation 140 to display an anterior-posterior ("AP") image adjacent to a lateral image of the same anatomy. In another example, a hanging protocol may direct display workstation 140 to display the AP image before displaying the lateral image. In general, a hanging protocol can dictate the spatial and/or temporal presentation of a plurality of images at display workstation 140.

A hanging protocol differs from a default display protocol ("DDP"). In general, a DDP is a default workflow that applies a series of image processing functions to image data. The image processing functions are applied to the image data in order to present an image (based on the image data) to a user.

The image processing functions alter the appearance of image data. For example, an image processing function may alter the contrast level of an image.

DDPs typically include processing steps or functions that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users.

Conversely, applying a hanging protocol to image data does not alter the appearance of an image (based on the image data), but instead dictates how the image(s) is(are) presented, as described above.

Server 130 can store a plurality of hanging protocols. The hanging protocols that are stored at server 130 and have not yet been modified or customized are default hanging protocols. A default hanging protocol can be selected from a plurality of default hanging protocols based on any number of relevant factors such as, for example, a manual selection of the default hanging protocol, a user identity, and/or pre-processing of the image data.

Specifically, a default hanging protocol may be selected based on a manual selection simply by communicating the default hanging protocol once a user has selected that particular protocol. The user can make the selection, for example, at a display workstation 140.

Server 130 includes a computer-readable storage medium. The storage medium can include a computer hard drive, a compact disc ("CD") drive, a USB thumb drive, or any other type of memory capable of storing one or more computer software applications. The storage medium includes a set of instructions for a computer. The set of instructions includes one or more routines capable of being run or performed by workstations 140. The set of instructions can be embodied in one or more software applications or in computer code. As described in more detail below, one technical effect of the set of instructions is to recommend, provide and/or adapt one or more hanging protocols or changes to hanging protocols to increase the efficiency of a user in reading an imaging study.

In one or more embodiments, the selection and modification of hanging protocols by a plurality of users is monitored and the results of this monitoring is used to recommend particular hanging protocols and hanging protocol modifications to one or more users in an effort to improve the efficiency of all users. For example, a first user can select a particular hanging protocol to review an imaging study from one of workstations 140. This selection of the hanging protocol can be monitored by one or more software applications running or operating on server 130 or some other computer device in communication with the user's workstation 140. In reviewing the images in the study, the first user can alter, or change the display rules of the hanging protocol to complete the user's review or diagnosis of the imaging study more accurately and efficiently. In addition, the first user can use other image processing tools to alter the presentation of images. For example, the first user can use tools such as image zoom, pan, contrast adjustment, adjustment of window level and/or cine, for example. The alterations or changes can also be monitored by one or more software applications running or operating on server 130 or some other computer device in communication with the user's workstation 140.

Several other items of information can also be monitored. For example, the number of images in the imaging study being examined by the first user, the number of groups of images in the imaging study being examined, the number of historical imaging studies reviewed during the first user's reading of the imaging study, the number of changes or alterations to the hanging protocol by the user and/or an amount of time required for the user to complete his or her reading of the imaging study can be monitored or tracked. Other additional information helpful to improve upon various users' efficiencies in reading imaging studies can also be tracked or monitored. In general, the information monitored is referred to as usage information.

Based at least in part on the information obtained during the monitoring, a productivity factor can be determined. For example, all or a portion of the information described above can be monitored for one or more of a plurality of users. This information can then be used to calculate a numerical factor for one more of the users. For example, the information can be used to determine an efficiency or productivity rating that indicates an efficiency of one user with respect to another. The factor or rating can vary across virtually any numerical range. For example, the factor or rating can vary between 0 and 1, 0 and 10, and 0 and 100, with 0 being the slowest, or least efficient and 1, 10 or 100 being the fastest, or more efficient.

One or more of the users can have this factor assigned to the usage information monitored. For example, if a given user selects a particular hanging protocol and uses the protocol to read an imaging study with X images in it, Y groups of images in it and Z historical imaging studies also reviewed during the reading, while making M changes to the hanging protocol and completing his/her reading in N minutes, the usage information monitored during this reading can be assigned a productivity factor of 0.4. If a second user selects the a different hanging protocol and uses the protocol to read an imaging study with (X+A) images in it, (Y−B) groups of images in it and (Z+C) historical imaging studies also reviewed during the reading, while making (M−D) changes to the hanging protocol and completing his/her reading in (N−E) minutes, the usage information monitored during this reading can be assigned a productivity factor of 0.7, for example. The variables A, B, C, D, M, N, X, Y and Z are used merely as examples of integers and are not intended to limit embodiments of the presently described technology.

Once the productivity factors are determined or calculated, they can be used to recommend a particular hanging protocol and/or one or more changes to the hanging protocol for a later user's reading of an imaging study. For example, based on productivity factors calculated for a plurality of users, a recommendation can be made to a later user as to which hanging protocol and/or which changes to a particular hanging protocol can be used to provide a more efficient reading of an imaging study. This recommendation can be based on the productivity factor alone, or on the productivity factor in combination with a comparison of the usage information monitored for one or more previous users and the current user. For example, if a current user is reading an imaging study with the same or similar number of images or groups of images (similar meaning a statistically insignificant difference in the numbers, such as 1-4%), the most efficient productivity factor calculated for other users who read an imaging study with the same/similar number of images/groups can be used to recommend the hanging protocol(s) and/or changes to hanging protocol(s) used by those users who generated the most efficient productivity factor. In doing so, the presently described technology provides an adaptive method for recommending a hanging protocol and/or changes to a protocol based on the efficiency of other users. In other words, the presently described technology helps inefficient, or less efficient users learn from more efficient users so that more users become increasingly efficient.

In operation, a first user employs workstation 140 to obtain a hanging protocol from server 130. This hanging protocol is referred to as a selected hanging protocol. A set of instructions for a computer stored on a computer-readable storage medium can operate to monitor usage information related to hanging protocols, determine a productivity factor and recommend a hanging protocol and/or change to a protocol to one or more users. The set of instructions can be embodied in one or more software routines or software applications, for example. The set of instructions can be stored at server 130 or any other computer readable storage medium.

The set of instructions can include a monitor routine. The monitor routine is configured to monitor usage information for hanging protocols. Usage information can include any information or data related to the selection of and/or changes to a hanging protocol. For example, the usage information can include data on the number of times a particular hanging protocol is selected, the types of imaging studies read using a particular hanging protocol and the types of diagnoses performed using a particular hanging protocol.

In another example, the usage information can include changes to a hanging protocol. For example, when a user reads an imaging study using a hanging protocol, the user may wish to make changes to the hanging protocol. A change can include an alteration of one or more display rules or order of display rules in the hanging protocol, for example.

The changes to a hanging protocol can be thought of as starting points for subprotocols. That is, each change to a hanging protocol begins a new subprotocol. In this way, a user begins reading an imaging study using a hanging protocol and begins a subprotocol each time the user makes a change to the hanging protocol.

In another example, the usage information includes image processing tools and/or parameters related to the image processing tools, such as image zoom, pan, contrast adjustment, window level adjustment and/or cine, for example. The type and/or degree/amount of the image processing tools can be monitored as usage information.

The usage information can also include other data related to the imaging studies read or examined using a particular hanging protocol and/or particular changes to the hanging protocol. For example, the usage information can include data related to the a number of images in the imaging study or studies being examined with the hanging protocols or subprotocols, the number of groups of images in the imaging study or studies being examined, the number of historical imaging studies reviewed during a user's reading of the imaging study or studies with the hanging protocol and/or subprotocols, the number of changes or subprotocols employed during a user's reading of the imaging study or studies and/or an amount of time required for a user to complete a reading of an imaging study or studies. The usage information can also include data on any additional information reviewed by a user in reading an imaging study or studies. For example, if the user reviews additional information about the patient or imaging modality during his or her reading of an imaging study, this additional information can be monitored or tracked by the monitor routine.

The monitor routine can monitor, or track, this usage information associated with a particular hanging protocol. The monitor routine can monitor this information via communication connections between server 130 and display workstations 140. For example, the monitor routine can monitor this information via one or more network and/or Internet connections.

The usage information monitored or tracked by the monitor routine can be stored on a computer readable storage medium. For example, the usage information can be recorded in a database at server 130 or one or more of display workstations 140.

The set of instructions can also include a productivity routine. The productivity routine determines a productivity factor. The productivity factor is representative of the efficiency of a user in reading or making a diagnosis based on an imaging study or studies using a particular hanging protocol and/or set of change(s) to the protocol (or, subprotocols). The productivity factor can vary based on the efficiency of different users using different hanging protocols and subprotocols. In other words, while two different users may both be equally adept and competent in their reading of a particular imaging study, the efficiencies of these users may differ based on each user employing different hanging protocols and subprotocols to read the imaging study. The productivity factor is a numerical indicator of this relative efficiency.

The productivity factor is used to determine whether the use of a particular hanging protocol, subprotocol, set of hanging protocols and/or set of subprotocols is more efficient than using a different hanging protocol, subprotocol, set of hanging protocols and/or set of subprotocols in reading an imaging study or type of imaging study. A "type" of imaging study can be a category of imaging study. For example, all imaging studies that include images obtained from a particular imaging modality can be included in one type of imaging studies. In another example, all imaging studies that include images of a particular body part or anatomy can be included in one type of imaging studies. In yet another example, all imaging studies that include images obtained from a particular imaging procedure can be included in one type of imaging studies. However, other types of imaging studies can be used in accordance with the embodiments of the presently described technology.

The productivity factor can be determined in any of a number of ways. For example, a productivity factor between 0 and 1, 0 and 10 or 0 and 100 based on the percentile rank of efficiencies among various hanging protocols, subprotocols, hanging protocol sets and/or subprotocol sets used to read an imaging study or type of imaging study. If a first hanging protocol, subprotocol, hanging protocol set and/or subprotocol set is more efficient than 99% of other hanging protocols, subprotocols, hanging protocol sets and/or subprotocol sets in reading an imaging study or type of imaging study, then the first protocol or protocol set can be assigned a productivity factor of 0.99, 9.9 or 99, for example. However, other ways to calculate a productivity factor can be used. For example, a productivity factor for a first hanging protocol can be twice as large as a productivity factor for a second hanging protocol if the first protocol is, or has been, twice as efficient as the second protocol in reading imaging studies.

The data used to generate or determine a productivity factor can include the usage information described above. For example, the number of images in an imaging study, number of groups of images in the imaging study, number of historical imaging studies reviewed during a reading of the imaging study, the number of changes to a selected hanging protocol (that is, subprotocols generated by a user) and/or an amount of time required to complete a reading of an imaging study using a hanging protocol, subprotocol or set of protocols/subprotocols can be used to determine a numerical productivity factor.

The productivity factors for various protocols, subprotocols and protocol/subprotocol sets can vary with time. That is, if the use of a particular set of subprotocols becomes more or less efficient in reading a type of imaging studies, then the productivity factor associated or calculated for that set of subprotocols can decrease, for example. In this way, the productivity factors can adapt to the changing efficiencies of users employing various protocols and subprotocol sets in reading imaging studies.

The productivity factors can be stored at a computer readable storage medium or memory such as a computer hard drive, for example (although other types of memory can also be used). For example, the productivity factors can be stored in a database or table at server 130 or at one or more workstations 140.

The set of instructions can also include a recommendation routine. The recommendation routine is configured to recommend a hanging protocol, subprotocol (or change to a hanging protocol), a set of hanging protocols or a set of subprotocols (or changes to a hanging protocol) to a user. For example, the recommendation routine can recommend a particular hanging protocol or change to a hanging protocol currently used by a user in reading an imaging study.

The recommendation routine recommends a protocol/subprotocol or set of protocols/subprotocols that can be more efficient in reading an imaging study or type of imaging study. For example, based on the imaging study or type of imaging study being read by a user, the recommendation routine can determine an efficient protocol/subprotocol or set of protocols/subprotocols for reading the imaging study.

In an embodiment, the recommendation routine makes a recommendation to a user before the user's reading of an imaging study begins. For example, once a user selects a hanging protocol to read an imaging study, the recommendation routine determines a hanging protocol, subprotocol, set of hanging protocols or set of subprotocols with a productivity factor that is greater (or more efficient) than the protocol selected by the user. In another example, once a user selects an imaging study to read, the recommendation routine determines a hanging protocol, subprotocol, set of hanging protocols or set of subprotocols with a productivity factor that is greater (or more efficient) than a predetermined threshold. While the recommendation routine can recommend the most efficient protocol, subprotocol or set of protocol/subprotocols (or that is associated with the greatest productivity factor), the recommendation routine can also recommend a protocol/subprotocol or protocol/subprotocol set that is not the most efficient.

In an embodiment of the presently described technology, the recommendation routine recommends a protocol/subprotocol or protocol/subprotocol set by causing a display device connected to a workstation 140 to visually present a button, icon or other geometric shape and/or text to a user. The user can then, using an input device such as a mouse, stylus, microphone or keyboard, select the shape and/or text to cause the recommended hanging protocol, subprotocol, set of hanging protocols or set of subprotocols to be activated, or used to read the imaging study.

Embodiments of the presently described technology can continue to adapt the changes to a hanging protocol (or subprotocols) employed by a user in reading an imaging study so that the user's efficiency is increased. For example, the recommendation routine can recommend a change to a hanging protocol employed by a user, or subprotocol, during the user's reading of an imaging study. That is, as the user reads an imaging study, the recommendation routine can continue to recommend the next change or subprotocol that is likely to increase the user's efficiency.

In an embodiment of the presently described technology, a productivity factor is determined for each of a plurality of users. The productivity factor is calculated by the productivity routine based on each user's efficiency in reading an imaging study or type of imaging study. The productivity factor can also be based on one or more items listed above as types of usage information. Once the productivity factors are determined, the recommendation routine can recommend a hanging protocol, subprotocol or set thereof to another user based on a comparison between that user's productivity factor and the productivity factors calculated for the plurality of users. In an embodiment, the hanging protocols and/or subprotocols used by one or more users with greater productivity factors than a current user are recommended to the current user by the recommendation routine.

FIGS. 2A and 2B illustrate a flowchart for a method 200 for adapting or recommending a hanging protocol based on the efficiencies of a plurality of users employing hanging protocols and/or subprotocols to read imaging studies, in accordance with an embodiment of the presently described technology. First, at step 210, usage information is monitored or tracked for a plurality of users during each user's reading of imaging studies. As described above, usage information can include a variety of information related to a user's reading of an imaging study with hanging protocols, changes to hanging protocols (or subprotocols) and/or sets of hanging protocols/subprotocols, for example.

Next, at step 220, productivity factors are determined or calculated for at least a plurality of the users monitored or tracked at step 210. As described above, the productivity factors can be calculated based on a variety of factors. In an example, a productivity factor is similar to a probability, "p." In other words, as a probability p can be calculated to determine the likelihood of a given event occurring, a productivity factor can be calculated to determine whether a particular combination of hanging protocols, set of hanging protocols, subprotocols and/or set of subprotocols is likely to be more efficient in reading an imaging study or type of imaging study than the currently used hanging protocol(s)/subprotocol(s). As described above, the productivity factor can be based on the usage information monitored/tracked at step 210 and a comparison between the efficiencies of a plurality of users in reading imaging studies with various hanging protocols/subprotocols combinations.

Next, at step 230, the hanging protocol or sets of protocols employed by a user in reading an imaging study is monitored or tracked. That is, the hanging protocol(s) assigned to or selected by a current user to read an imaging study is monitored.

Next, at step 240, a determination is made as to whether the hanging protocol(s) assigned to or selected by the current user in step 230 is less efficient for reading the imaging study or type of imaging study being read by the user than one or more hanging protocols associated with the productivity factors calculated/determined at step 220, as described above. That is, a determination is made as to whether the combination of the imaging study (or type of imaging study) being read by a current user and the hanging protocol(s) employed by the current user is likely to be less efficient than one or more productivity factors calculated at step 230. In an embodiment of the presently described technology, step 240 can include calculating a productivity factor for the current user based on the usage information related to the current user's reading of an imaging study. The newly calculated productivity factor can then be compared to one or more of the productivity factors determined/calculated at step 220 to determine if another hanging protocol and imaging study combination is likely more efficient, for example.

If it is determined that the hanging protocol(s) employed by the current user is less efficient that one or more of the productivity factors at step 240, method 200 proceeds from step 240 to step 250. At step 250, at least one of the hanging protocol(s) associated with one or more of the productivity factors determined to be more efficient (at step 240) is recommended to the current user, as described above. If the user selects the recommended hanging protocol(s), the selected hanging protocol(s) are applied to the imaging study to assist the user in reading the imaging study. In this way, method 200 can be used to recommend a more efficient hanging protocol or set of hanging protocols to a user than the hanging protocol(s) employed by the user prior to reading an imaging study, for example. Method 200 next proceeds from step 250 to step 260.

If it is determined that the hanging protocol(s) employed by the current user is not less efficient that one or more of the productivity factors at step 240, method 200 proceeds from step 240 to step 260. At step 260, the usage information associated with a user reading an imaging study is monitored or tracked as the user reads the imaging study, as described above. For example, a user's changes to a hanging protocol can be monitored during that user's reading of the imaging study.

From step 260, method 200 proceeds to step 270. At step 270, a determination is made as to whether a subprotocol or set of subprotocols employed by the current user is less efficient than a productivity factor calculated/determined at step 220. That is, as the current user adapts or makes changes to a hanging protocol during his/her reading of an imaging study, a determination is made as to whether a more efficient combination of subprotocols is likely to be more efficient. This determination can be made, for example, by determining a productivity factor for the current user and comparing this productivity factor to one or more of the factors determined at step 220. If one or more productivity factors from step 220 is greater than the current user's productivity factor (or likely to be more efficient in reading the imaging study or type of imaging study being read by the current user), method 200 proceeds from step 270 to step 280. If the productivity factors from step 220 are not greater than the current user's productivity factor (or not likely to be more efficient in reading the imaging study or type of imaging study being read by the current user), method 200 proceeds from step 270 to step 290.

At step 280, one or more subprotocols or sets of subprotocols associated with a productivity factor greater than the current user's productivity factor is recommended to the current user, as described above. If the current user selects the recommended subprotocol(s), the subprotocol(s) are then applied to the imaging study to assist the user in reading the imaging study.

At step 290, a determination is made as to whether the current user has completed his/her reading of the imaging study. For example, a determination can be made as to whether the current user has made a diagnosis based on the imaging study. If the current user has completed his/her reading, method 290 proceeds from step 290 to step 295, where method 200 terminates. If the current user has not completed his/her reading, method 290 proceeds from step 290 to step 270.

Figure 3:
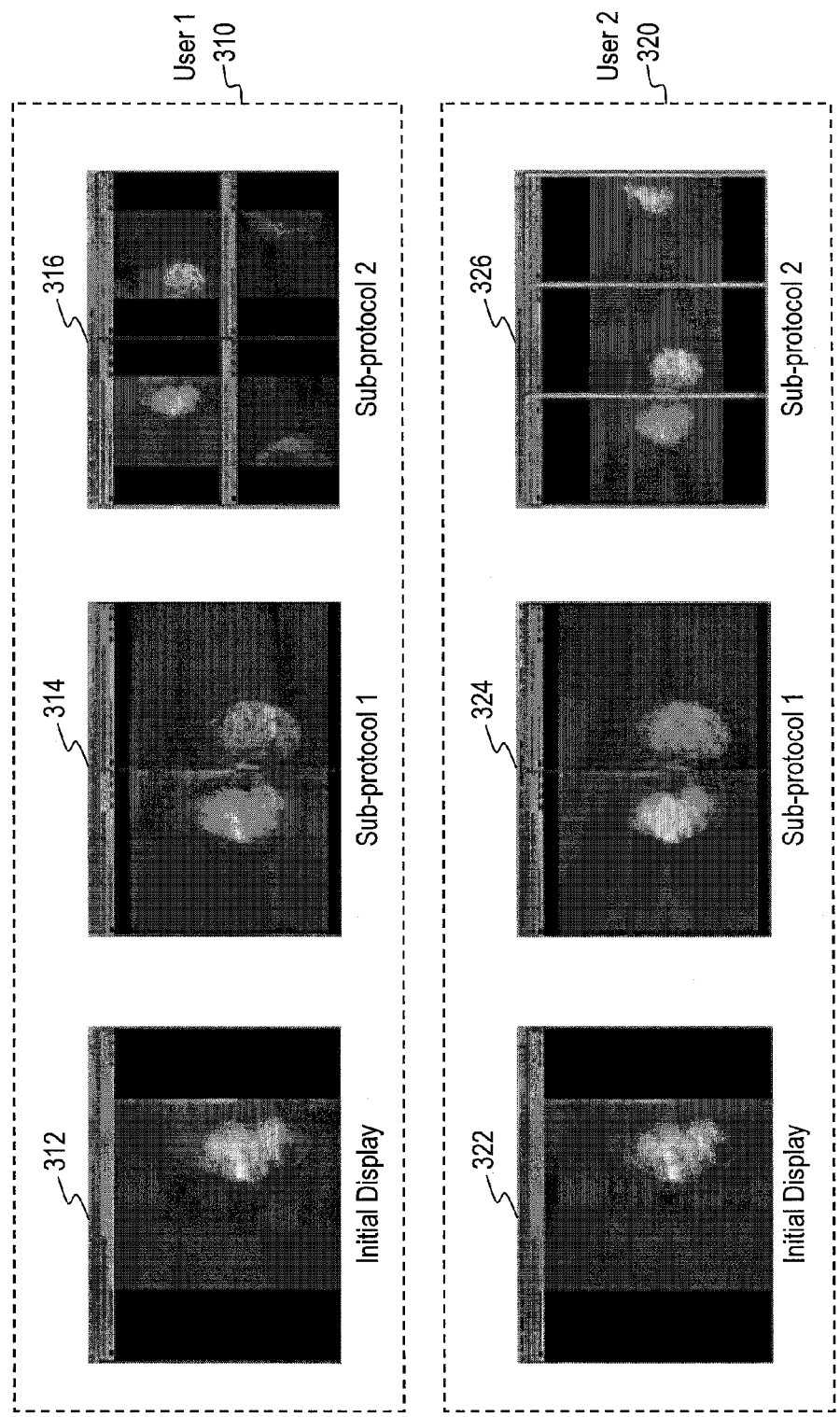
FIG. 3 illustrates a schematic diagram of an example embodiment of the presently described technology.

FIG. 3 illustrates a schematic diagram of an example embodiment of the presently described technology. FIG. 3 includes a hanging protocol 310, 320 with changes, or subprotocols, for reading an imaging study by each of two users, User 1 and User 2. In this example, each of User 1 and User 2 employed a hanging protocol with different changes, or subprotocols, to read the images in the same imaging study. The hanging protocol used by both User 1 and User 2 initially presented the first image of the imaging study using an initial display rule, resulting in displays 312, 322 for each user, respectively.

As described above, during each user's reading of the imaging study, their respective changes to the hanging protocol can be monitored by monitor routine, as described above. For example, each of User 1 and User 2 can decide to change the hanging protocol to cause displays 314, 324 to be displayed. Following the second displays 314, 324, User 1 changes the hanging protocol to cause display 316 to be presented and User 2 changes the hanging protocol to cause display 326 to be displayed.

During each users reading of the imaging study, monitor routine can track User 1's and User 2's changes to the hanging protocol. Based on one or more of the efficiency factors described above (including, for example, the number of images in the imaging study, the number of groups of images in the imaging study, the number of historical imaging studies reviewed during the reading of the imaging study, the particular hanging protocol selected, the number of changes to the hanging protocol (or subprotocols) and the time required to complete the reading of the imaging study), the productivity routine can calculate a productivity factor for each of User 1 and User 2. If User 1's subprotocols are determined to be associated with a higher productivity factor for reading the type of imaging study presented in FIG. 3 (compared to User 2), then the recommendation routine can recommend the hanging protocol 310 and subprotocols 312, 314, 316 used by User 1 to subsequent users who read the same type of imaging study. Conversely, as User 2's subprotocols are determined to be associated with a lower productivity factor compared to User 1, recommendation routine does not recommend the hanging protocol 320 and subprotocols 322, 324, 326 used by User 2 to subsequent users who read the same type of imaging study, for example.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for adapting a hanging protocol recommendation based on an efficiency of use, said method including:

monitoring usage information for a hanging protocol, said usage information including a selection of a hanging protocol and a change to said hanging protocol by a first experienced user during a reading of a medical imaging study, wherein said monitoring includes monitoring said usage information for one or more of an imaging modality used to obtain an image in said imaging study, an anatomy imaged in said imaging study, and an imaging procedure employed to obtain said image in said imaging study;

automatically dividing said hanging protocol into a sequence of a plurality of sub-protocols associated with said hanging protocol based on changes made by the first experienced user throughout the first experienced user's reading of said imaging study;

determining a productivity factor based on a comparison of an efficiency of said first experienced user during said reading of said imaging study with an efficiency of at least a second experienced user in a user population, said second experienced user also having made changes to said hanging protocol, the productivity factor associated with said hanging protocol and varying over time to adapt to changing efficiencies of the user population;

comparing usage information monitored for said first experienced user with usage information monitored for a less experienced user; and adaptively recommending application of said hanging protocol including associated sub-protocols in said sequence to said less experienced user based on said productivity factor and said comparing of monitored user usage information.

2. The method of claim 1, wherein said change to said hanging protocol includes information reviewed by said first user in addition to said imaging study during said reading.

3. The method of claim 2, wherein said information includes one or more historical imaging studies.

4. The method of claim 1, wherein said efficiency is based on at least one of:
(a) a number of images in said imaging study;
(b) a number of groups of said images in said imaging study;
(c) a number of historical imaging studies reviewed during said reading of said imaging study;
(d) said selection of said hanging protocol;
(e) a number of said changes to said hanging protocol; and
(f) a time required to complete said reading of said imaging study.

5. The method of claim 1, wherein said recommending step occurs during a reading of a second imaging study by said less experienced user.

6. The method of claim 1, wherein said recommending step includes recommending application of said hanging protocol including associated sub-protocols in said sequence to said less experienced user based on said imaging modality, said anatomy and said imaging procedure.

7. The method of claim 1, wherein said monitoring and determining steps occur for a plurality of users and said recommending step includes recommending application of said hanging protocol including associated sub-protocols in said sequence based on a comparison between one or more productivity factors of said plurality of users and a productivity factor of said less experienced user.

8. A non-transitory computer-readable storage medium comprising a set of instructions for a computer, said set of instructions including:

a monitor routine configured to monitor usage information for a hanging protocol, said usage information including a selection of a hanging protocol and a change to said hanging protocol by a first experienced user during a reading of a medical imaging study, and dividing said hanging protocol into a sequence of a plurality of sub-protocols associated with said hanging protocol based on changes made by the first experienced user throughout the first experienced user's reading of said imaging study, wherein said monitor routine is configured to monitor said usage information for one or more of an imaging modality used to obtain an image in said imaging study, an anatomy imaged in said imaging study, and an imaging procedure employed to obtain said image in said imaging study;

a productivity routine configured to determine a productivity factor based on a comparison of an efficiency of said first experienced user during said reading of said imaging study with an efficiency of at least a second experienced user in a user population, said second experienced user also having made changes to said hanging protocol, the productivity factor associated with said hanging protocol and varying over time to adapt to changing efficiencies of the user population, and comparing usage information monitored for said first experienced user with usage information monitored for a less experienced user; and a recommendation routine configured to adaptively recommend application of said hanging protocol including associated sub-protocols in said sequence to a said less experienced user based on said productivity factor and said comparing of monitored user usage information.

9. The non-transitory computer-readable storage medium of claim 8, wherein said change to said hanging protocol includes information reviewed by said first experienced user in addition to said imaging study during said reading.

10. The non-transitory computer-readable storage medium of claim 9, wherein said information includes one or more historical imaging studies.

11. The non-transitory computer-readable storage medium of claim 8, wherein said efficiency is based on at least one of:
(a) a number of images in said imaging study;
(b) a number of groups of said images in said imaging study;
(c) a number of historical imaging studies reviewed during said reading of said imaging study;
(d) said selection of said hanging protocol;
(e) a number of said changes to said hanging protocol; and
(f) a time required to complete said reading of said imaging study.

12. The non-transitory computer-readable storage medium of claim 8, wherein said recommendation routine is configured to recommend application of said hanging protocol including associated sub-protocols in said sequence during a reading of a second imaging study by said less experienced user.

13. The non-transitory computer-readable storage medium of claim 8, wherein said recommendation routine is configured to recommend application of said hanging protocol including associated sub-protocols in said sequence to said less experienced user based on said imaging modality, said anatomy and said imaging procedure.

14. The non-transitory computer-readable storage medium of claim 8, wherein said monitor routine is configured to monitor said usage information and said productivity routine is configured to determine said productivity factor for a plurality of users and said recommendation routine is configured to recommend protocol including associated sub-protocols in said sequence based on a comparison between one or more productivity factors of said plurality of users and a productivity factor of said less experienced user.

* * * * *